US012652273B2

(12) United States Patent
Arora et al.

(10) Patent No.: US 12,652,273 B2
(45) Date of Patent: Jun. 9, 2026

(54) ENCRYPTING DATA GENERATED FROM MEDICAL DEVICES

(71) Applicant: MONOVO, LLC, Orem, UT (US)

(72) Inventors: Siddhartha Arora, Orem, UT (US); Adam Quillan Ure, Orem, UT (US)

(73) Assignee: Monovo, LLC

( * ) Notice: Subject to any disclaimer, the term of this patent is extended or adjusted under 35 U.S.C. 154(b) by 12 days.

(21) Appl. No.: 18/705,478

(22) PCT Filed: Oct. 27, 2022

(86) PCT No.: PCT/US2022/048011
§ 371 (c)(1),
(2) Date: Apr. 26, 2024

(87) PCT Pub. No.: WO2023/076467
PCT Pub. Date: May 4, 2023

(65) Prior Publication Data
US 2025/0021688 A1     Jan. 16, 2025

Related U.S. Application Data

(60) Provisional application No. 63/272,413, filed on Oct. 27, 2021, provisional application No. 63/272,428, (Continued)

(51) Int. Cl.
*H04L 9/40*        (2022.01)
*A61B 5/00*        (2006.01)
(Continued)

(52) U.S. Cl.
CPC ........ *H04L 63/0428* (2013.01); *A61B 5/0002* (2013.01); *A61B 5/6801* (2013.01); *G06F 21/6245* (2013.01); *H04L 9/321* (2013.01)

(58) Field of Classification Search
CPC ............. H04L 9/32–3213; H04L 63/04; H04L 63/0428; H04L 63/08; H04L 63/0861;
(Continued)

(56) References Cited

U.S. PATENT DOCUMENTS 12,126,995 B2 *   10/2024   Hua ....................... G16H 40/67
2003/0130590 A1     7/2003   Bui et al.
(Continued)

FOREIGN PATENT DOCUMENTS

WO      2018/046742       3/2018
WO      2020/049267 A1    3/2020

OTHER PUBLICATIONS

International Preliminary Report on Patentability received for PCT Patent Application No. PCT/US2022/047997, mailed on May 10, 2024, 13 pages.
(Continued)

*Primary Examiner* — Boris D Grijalva Lobos
(74) *Attorney, Agent, or Firm* — Workman Nydegger

(57) ABSTRACT

A cloud service is configured to receive a request from a mobile device requesting for authenticating the mobile device for receiving personal health data from a wearable device that is registered with the cloud service. In response to successful authentication, the cloud service sends a secondary character to the mobile device, which in turn passes the secondary character to the wearable device. In response to successful verification of the secondary character, the cloud service receives encrypted personal health data generated from the mobile device. The cloud service stores the encrypted personal health data at rest. When the cloud service provides the personal health data to a user, the cloud service decrypts the data and re-encrypts it with a different encryption mechanism, and sends the re-encrypted data to the user.

13 Claims, 5 Drawing Sheets

Related U.S. Application Data filed on Oct. 27, 2021, provisional application No. 63/272,529, filed on Oct. 27, 2021, provisional application No. 63/272,552, filed on Oct. 27, 2021, provisional application No. 63/272,431, filed on Oct. 27, 2021, provisional application No. 63/272,545, filed on Oct. 27, 2021, provisional application No. 63/272,553, filed on Oct. 27, 2021.

(51) Int. Cl.
  *G06F 21/62* (2013.01)
  *H04L 9/32* (2006.01)

(58) Field of Classification Search
  CPC .. G06F 21/6245; A61B 5/0002; A61B 5/6801
  See application file for complete search history.

(56) References Cited

U.S. PATENT DOCUMENTS

| | | |
|---|---|---|
| 2013/0151166 A1 | 6/2013 | Snyder |
| 2014/0163393 A1 | 6/2014 | Mccombie et al. |
| 2015/0025394 A1 | 1/2015 | Hong et al. |
| 2015/0269355 A1* | 9/2015 | Tidor .................... G16H 10/20 |
| | | 705/3 |
| 2017/0000347 A1 | 1/2017 | Meftah et al. |
| 2017/0068785 A1* | 3/2017 | Experton ............. H04W 12/02 |
| 2017/0249434 A1 | 8/2017 | Brunner |
| 2018/0026973 A1* | 1/2018 | Le Saint .............. H04W 12/06 |
| 2018/0116598 A1 | 5/2018 | Lee et al. |
| 2018/0303419 A1 | 10/2018 | Munoz et al. |
| 2018/0353137 A1 | 12/2018 | Balajadia et al. |
| 2019/0150778 A1 | 5/2019 | Li et al. |
| 2019/0207927 A1* | 7/2019 | Lakhani ................. G06F 21/42 |
| 2020/0357517 A1 | 11/2020 | Haddad et al. |
| 2020/0388397 A1 | 12/2020 | Shoaran et al. |
| 2021/0104304 A1 | 4/2021 | Davidovics et al. |
| 2021/0244281 A1 | 8/2021 | Cloward et al. |
| 2022/0223242 A1* | 7/2022 | McFarlane ............. G06Q 20/40 |
| 2023/0240529 A1* | 8/2023 | Toth .................... G06F 11/3006 |
| | | 600/301 |
| 2023/0315875 A1* | 10/2023 | Hansen ................... H04L 9/008 |
| | | 726/26 |
| 2024/0048539 A1* | 2/2024 | Nguyen ................... H04L 9/14 |
| 2025/0009226 A1 | 1/2025 | Shurtliff et al. |
| 2025/0228457 A1 | 7/2025 | Taylor et al. |
| 2025/0239361 A1 | 7/2025 | Taylor et al. |

OTHER PUBLICATIONS

International Preliminary Report on Patentability received for PCT Patent Application No. PCT/US2022/048004, mailed on May 10, 2024, 10 pages.
International Preliminary Report on Patentability received for PCT Patent Application No. PCT/US2022/048006, mailed on May 10, 2024, 13 pages.
International Preliminary Report on Patentability received for PCT Patent Application No. PCT/US2022/048011, mailed on Feb. 1, 2023, 10 pages.
International Preliminary Report on Patentability received for PCT Patent Application No. PCT/US2022/048011, mailed on May 10, 2024, 08 pages.
International Search Report and Written Opinion received for PCT Patent Application No. PCT/US2022/047997, mailed on Feb. 14, 2023, 16 pages.
International Search Report and Written Opinion received for PCT Patent Application No. PCT/US2022/048004, mailed on Mar. 16, 2023, 14 pages.
International Search Report and Written Opinion received for PCT Patent Application No. PCT/US2022/048006, mailed on Feb. 16, 2023, 16 pages.
International Search Report and Written Opinion for PCT/US2022/048011 mailed Feb. 1, 2023.
Non-Final Office Action received for U.S. Appl. No. 18/705,439, mailed on Mar. 24, 2026, 19 pages.

* cited by examiner

ENCRYPTING DATA GENERATED FROM MEDICAL DEVICES

CROSS-REFERENCE TO RELATED APPLICATION

The present invention is a 35 U.S.C. § 371 U.S. National Stage of PCT Application No. PCT/US2022/048011, filed on Oct. 27, 2022, which_claims priority to and the benefit of United States Provisional Patent Application Numbers: 63/272,431, filed Oct. 27, 2021; 63/272,529, filed Oct. 27, 2021; 63/272,413, filed Oct. 27, 2021; 63/272,545, filed Oct. 27, 2021; 63/272,552, filed Oct. 27, 2021; 63/272,553, filed Oct. 27, 2021; and 63/272,428, filed Oct. 27, 2021. Each of the foregoing applications is incorporated herein by reference in its entirety.

BACKGROUND

Personal health data (PHI) is protected under Health insurance Portability and Accountability Act (HIPAA) privacy rule. However, much of the PHI data is generated by medical devices. When the PHI data associated with a patient is generated by a medical device, the medical device stores such PHI data in internal storage or transmits the PHI data to another device via wired communication or wireless communication.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

The embodiments described herein are related to encrypting personal health data generated by medical devices regardless of whether the personal health data is in transmission or at rest. In some embodiments, the encrypting of personal health data and transmitting of encrypted personal health data may be performed by a system, including a service computer system, a wearable device, and a mobile device. The service computer system is configured to register a plurality of wearable devices. The service computer system (e.g., a cloud server) is configured to receive a request from a mobile device, requesting for authenticating the mobile device. The authenticated mobile device is configured to receive personal health data from a wearable device that is registered with the service computer system.

The request includes a wearable device identifier, a mobile device identifier, and a user identifier. In response to successfully authenticating the request, the service computer system sends a secondary character to the mobile device, which in turn passes the secondary character to the wearable device. In response to receiving the secondary character, the wearable device is then caused to encrypt a set of personal health data and send the set of encrypted personal health data to the mobile device. In response to receiving the set of encrypted personal health data, the mobile device is then caused to pass the set of encrypted personal health data to the service computer system. The service computer system then receives the encrypted personal health data from the mobile device and stores the encrypted personal health data as encrypted data at rest.

The service computer system is further configured to provide a role-based portal to users having a plurality of roles. In some embodiments, the plurality of roles include (1) an admin role, (2) a clinical role, (3) a patient role, and (4) a reviewer role. Each of the plurality of roles is given a different scope of permission in operating on a different portion of personal health data. In some embodiments, the role-based portal provides a web application configured to allow users having the plurality of roles to access personal health data at a web browser.

In some embodiments, the role-based portal is configured to receive a request for personal health data from a user having a particular role among the plurality of roles at a web browser. The service computer system is configured to authenticate the request based on a user identifier and a device identifier and provides the requested personal health data to the web browser. In some embodiments, the device identifier is associated with a browser of a device that executes a web application.

In some embodiments, providing the requested personal health data to the web browser includes decrypting encrypted personal health data by a wearable device via a first encryption mechanism and re-encrypting the decrypted personal health data via a second encryption mechanism; and sending the re-encrypted personal health data to the web browser. The web browser is configured to decrypt the re-encrypted personal health data and display the decrypted personal health data in the web browser.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims or may be learned by the practice of the invention as set forth hereinafter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not, therefore, to be considered to be limiting in scope, embodiments will be described and explained with additional specificity and details through the use of the accompanying drawings in which.

DETAILED DESCRIPTION

Figure 1:
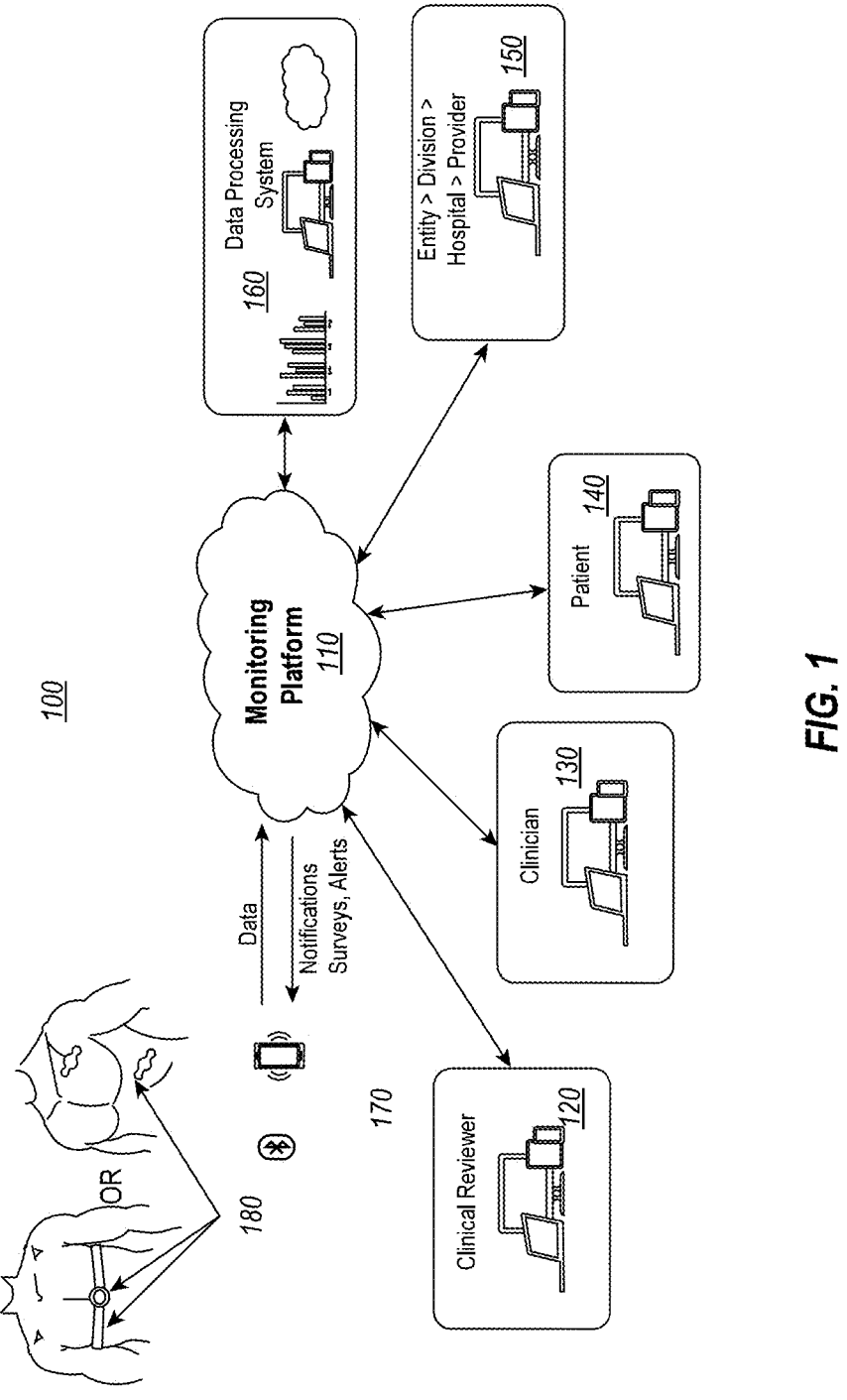
FIG. 1 illustrates an example of an environment in which the principles described herein may be implemented.

The embodiments described herein are related to encrypting personal health data generated by medical devices regardless of whether the personal health data is in transmission or at rest. In some embodiments, the encrypting of personal health data and transmitting of encrypted personal health data may be performed by a system, including a service computer system, a wearable device, and a mobile device. The service computer system is configured to register a plurality of wearable devices. The service computer system (e.g., a cloud server) is configured to receive a request from a mobile device, requesting for authenticating the mobile device. The authenticated mobile device is configured to receive personal health data from a wearable device that is registered with the service computer system.

The request includes a wearable device identifier, a mobile device identifier, and a user identifier. In response to successfully authenticating the request, the service computer system sends a secondary character to the mobile device, which in turn passes the secondary character to the wearable device. In response to receiving the secondary character, the wearable device is then caused to encrypt a set of personal health data and send the set of encrypted personal health data to the mobile device. In response to receiving the set of encrypted personal health data, the mobile device is then caused to pass the set of encrypted personal health data to the service computer system. The service computer system then receives the encrypted personal health data from the mobile device and stores the encrypted personal health data as encrypted data at rest.

The service computer system is further configured to provide a role-based portal to users having a plurality of roles. In some embodiments, the plurality of roles include (1) an admin role, (2) a clinical role, (3) a patient role, and (4) a reviewer role. Each of the plurality of roles is given a different scope of permission in operating on a different portion of personal health data. In some embodiments, the role-based portal provides a web application configured to allow users having the plurality of roles to access personal health data at a web browser.

In some embodiments, the role-based portal is configured to receive a request for personal health data from a user having a particular role among the plurality of roles at a web browser. The service computer system is configured to authenticate the request based on a user identifier and a device identifier and provides the requested personal health data to the web browser.

In some embodiments, providing the requested personal health data to the web browser includes decrypting encrypted personal health data by a wearable device via a first encryption mechanism and re-encrypting the decrypted personal health data via a second encryption mechanism; and sending the re-encrypted personal health data to the web browser. The web browser is configured to decrypt the re-encrypted personal health data and display the decrypted personal health data in the web browser.

FIG. 1 illustrates an example of an environment 100 in which the principles described herein may be implemented. The environment 100 includes a monitoring platform 110 (which is a cloud service) configured to communicate with users having a plurality of roles, including (but not limited to a device associated to clinical reviewer 120, clinician 130, patient 140, hospital 150, healthcare provider 150, etc. The monitoring platform 110 is also configured to receive data from a mobile device 170. The mobile device 170 is configured to receive personal health data from a wearable device 180 that is worn by a patient. Most importantly, the whole ecosystem causes the personal health data to be encrypted at all times, including at rest and in transition. Furthermore, the personal health data generated by different wearable devices is encrypted by different encryption keys. Thus, when one device is compromised, the personal health data generated by the rest of the wearable devices is still intact.

Figure 2:
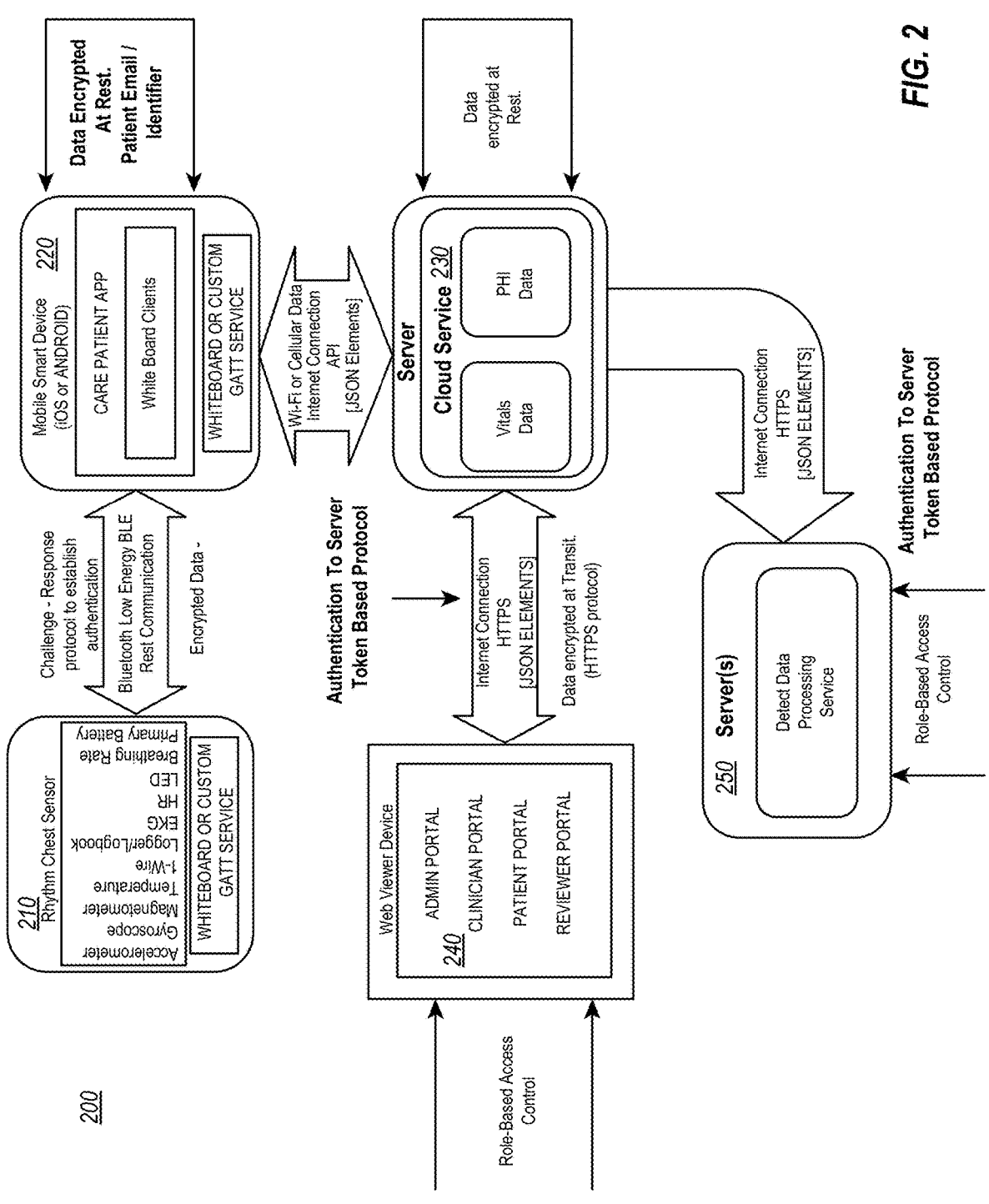
FIG. 2 illustrates a dataflow associated with the wearable device, a mobile device of a wearer, a cloud service, and a data processing service.

FIG. 2 illustrates a data flowchart illustrating an example of data flow among a wearable device 210 (e.g., chest sensor), a smart mobile device 220 (which corresponds to the mobile device 170 of FIG. 1), a cloud service 230 (which corresponds to the monitoring platform 110 of FIG. 1), and a data processing service 250 (which corresponds to the data processing system 160 of FIG. 1). The web viewer device 240 corresponds to the clinical reviewer 120, clinician 130, patient 140, and provider 150 portals of FIG. 1.

As illustrated in FIG. 2, the wearable device 210 (e.g., a chest sensor) is configured to generate personal health data of a wearer and encrypt the generated personal health data. The smart mobile device 220 (which may be an iOS device or an ANDROID device) has a care patient app installed thereon configured to communicate with the cloud service 230 and the wearable device 210. The wearable device 210 is registered with the cloud service. In some embodiments, the smart mobile device 220 is configured to be paired with the wearable device 210 via Bluetooth connection.

When the smart mobile device 220 is paired with the wearable device 210, the smart mobile device 220 can request personal health information from the wearable device 210. In some embodiments, the wearable device 210 and the smart mobile device 220 use a challenge-response protocol to establish authentication. For example, receiving the request, the wearable device 210 sends its identifier and a challenge to the smart mobile device 220. In response to receiving the identifier and the challenge, the smart mobile device 210 sends the wearable device identifier, its own identifier, and a user's identifier to the cloud service 230 for authentication. In response to successful authentication, the cloud service 230 sends the smart mobile device 220 a secondary character (e.g., a token), and the smart mobile device 220 passes the secondary character to the wearable device 210 as a response. After a successful authentication, the wearable device 210 encrypts a set of personal health data via an encryption key associated with the wearable device 210 and sends the encrypted set of personal health data to the smart mobile device 220. Receiving the encrypted set of personal health data, the smart mobile device 220 passes the encrypted personal health data to the cloud service 230.

As illustrated, the smart mobile device 220 keeps the data encrypted at rest with the user's email and/or identifier. In some embodiments, the smart mobile device 220 does not have access to the encryption key or decryption key of the wearable device 210, such that the smart mobile device 220 cannot read the encrypted data received from the wearable device 210 directly. In some embodiments, a copy of the encryption key of the wearable device 210 is stored at the cloud service 230. Thus, when the cloud service 230 receives the encrypted personal health data, the cloud service 230 is able to decrypt it. In some embodiments, the cloud service 230 keeps the data encrypted at rest. In some embodiments, the cloud service 230 only decrypts a portion of personal health data in response to a need-based request.

As briefly discussed with respect to FIG. 1, the cloud service 230 may provide a role-based portal to users having a plurality of roles. For example, there may be an admin portal, a clinician portal, a patient portal, a reviewer portal, etc. Users with each of the plurality of roles are given different scopes of permissions. For example, a patient may not be allowed to alter personal health data, while a doctor may be able to enter additional personal health data into the system. When personal health data is received from a wearable device, the cloud service 230 also provides such data to different users via different portals.

When a user at a portal portion 240 requests access to personal health data, the cloud service 230 first authenticates the user and user device. In response to successful authentication, the cloud service retrieves the wearable device's key and decrypts the portion of personal health data that was encrypted by the wearable device's key. The cloud service then re-encrypts the portion of personal health data via a different encryption mechanism, which the user device or browser is able to decrypt. For example, the different encryption mechanism may be HTTPS protocol.

Notably, the encrypted data may be tampered during the transmission. To detect tampering, in some embodiments, the encrypted data may be signed by each transmitting device. Alternatively, or in addition, in some embodiments, the encrypted data is hashed via a predetermined cryptographic hashing algorithm to generate a hash, e.g., SHA-256. The hash is appended to the encrypted data during transmission. For example, when the wearable device 210 sends a portion of encrypted personal health data, the encrypted personal health data may be hashed using a cryptographic hashing algorithm, such as SHA-256, to generate a hash. The hash is appended to the encrypted personal health data and transmitted to different devices. The hash can later be verified by a receiver of the encrypted data to prove that the data has not been tampered. For example, when the web viewer device 240 receives the encrypted personal health data, the web viewer device 240 can rehash the encrypted data using the same cryptographic hashing algorithm to generate a new hash. The new hash may then be compared with the hash that is appended to the encrypted health data. If the new hash matches the received hash, it indicates that the health data has not been tampered. If the new hash does not match the received hash, it indicates that the health data has been tampered.

Furthermore, in some embodiments, the cloud service 230 is also configured to anonymize the personal health data. The anonymization process may be performed while the data is encrypted or decrypted. Once the personal health data is anonymized, the cloud service 230 may transmit the anonymized health data to the data processing service 250 for further analysis. The data processing service 250 may also provide another set of role-based access control.

Figure 3:
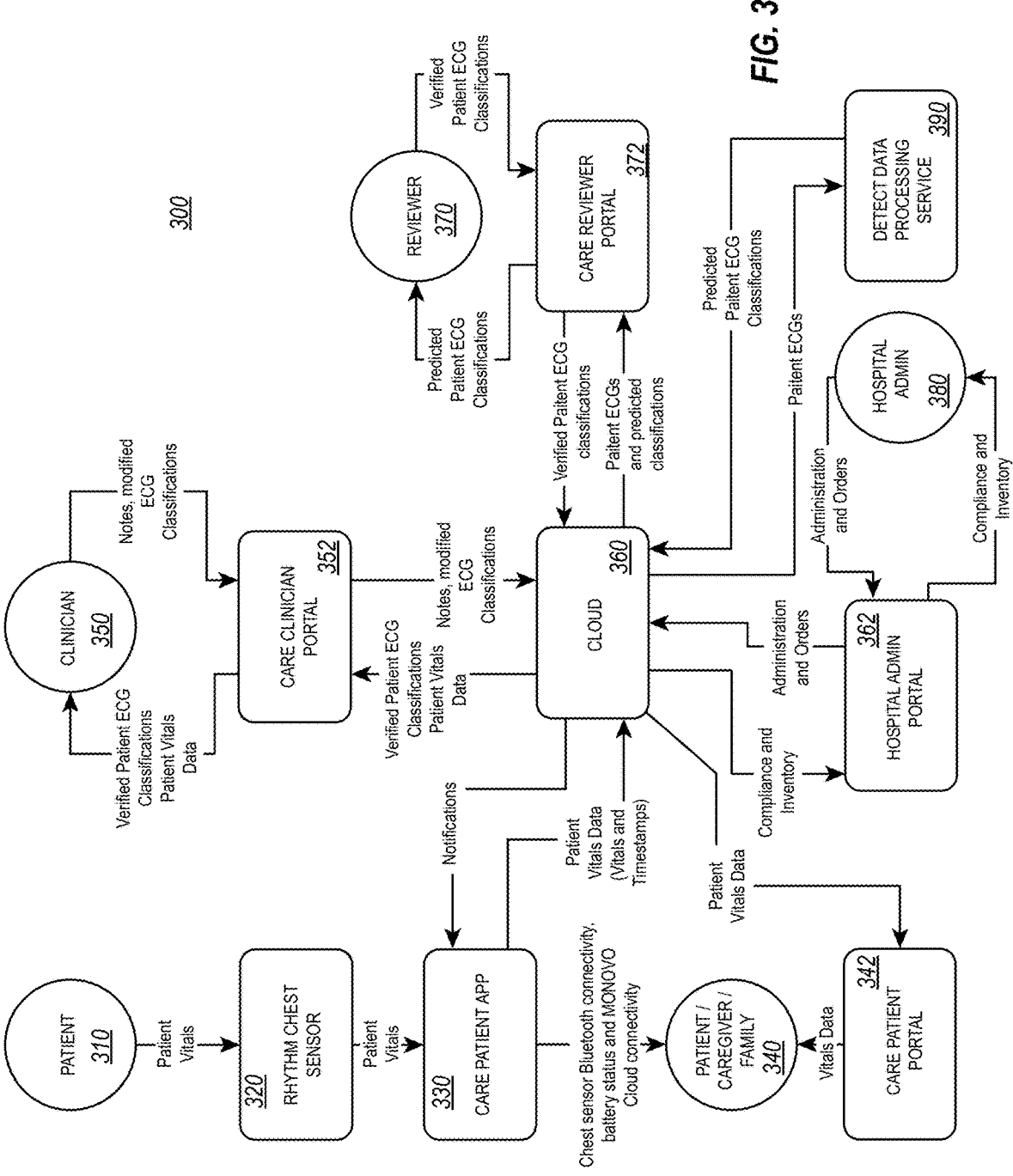
FIG. 3 illustrates a flowchart of role-based portal provided to users having a plurality of roles.

FIG. 3 is a flowchart 300 illustrating potential communications among a cloud service, a mobile app, a wearable device, and different portals. As illustrated, a patient 310 may be wearing a wearable device 320 (e.g., a chest sensor), which gathers patient personal health data (e.g., vitals). The personal health data (e.g., vitals) is first encrypted, and the encrypted personal health data is then sent to a care patient app 330 installed at a mobile device of the patient, which corresponds to the smart mobile device 220 of FIG. 2. The mobile app 330 is then configured to transmit the patient's personal health data to a cloud service 360, which corresponds to the cloud service 230 of FIG. 2. The cloud service 360 may transmit the health data to a data processing service 390, which corresponds to the data processing service 250 of FIG. 2.

After receiving the patient's personal health data, the cloud service 360 stores the personal health data securely (e.g., encrypted at rest). The cloud service 360 also provides role-based portals that provide different portions of personal health data to different users having different roles. For example, the role-based portals may include a care clinician portal 352 configured to provide patient ECG classifications and patient vitals data to a clinician 350, and the clinician is allowed to modify ECG classifications and add notes to the patient file. The role-based portals may also include a hospital admin portal 362 configured to allow hospital admin 380 to receive compliance and inventory-related data and generate administration and orders. The role-based portals may also include a care reviewer portal 372 configured to allow reviewers 370 to obtain predicted patient ECG classifications and generate verified patient ECG classifications. The role-based portals may also include a care patient portal 342 that allows patients and caregivers or family members 340 to review vital data. In some embodiments, the cloud service 360 is also configured to transmit the health data to the data processing service 390. The data processing service 390 is configured to further analyze the received health data. In some embodiments, the data processing service 390 implements different machine learning techniques, and uses the received data to train artificial intelligence (AI) models. In some embodiments, the data processing service 390 uses machine-learned AI models to perform diagnoses based on the health data of a particular patient.

The following discussion now refers to a number of methods and method acts that may be performed. Although the method acts may be discussed in a certain order or illustrated in a flow chart as occurring in a particular order, no particular ordering is required unless specifically stated, or required because an act is dependent on another act being completed prior to the act being performed.

Figure 4:
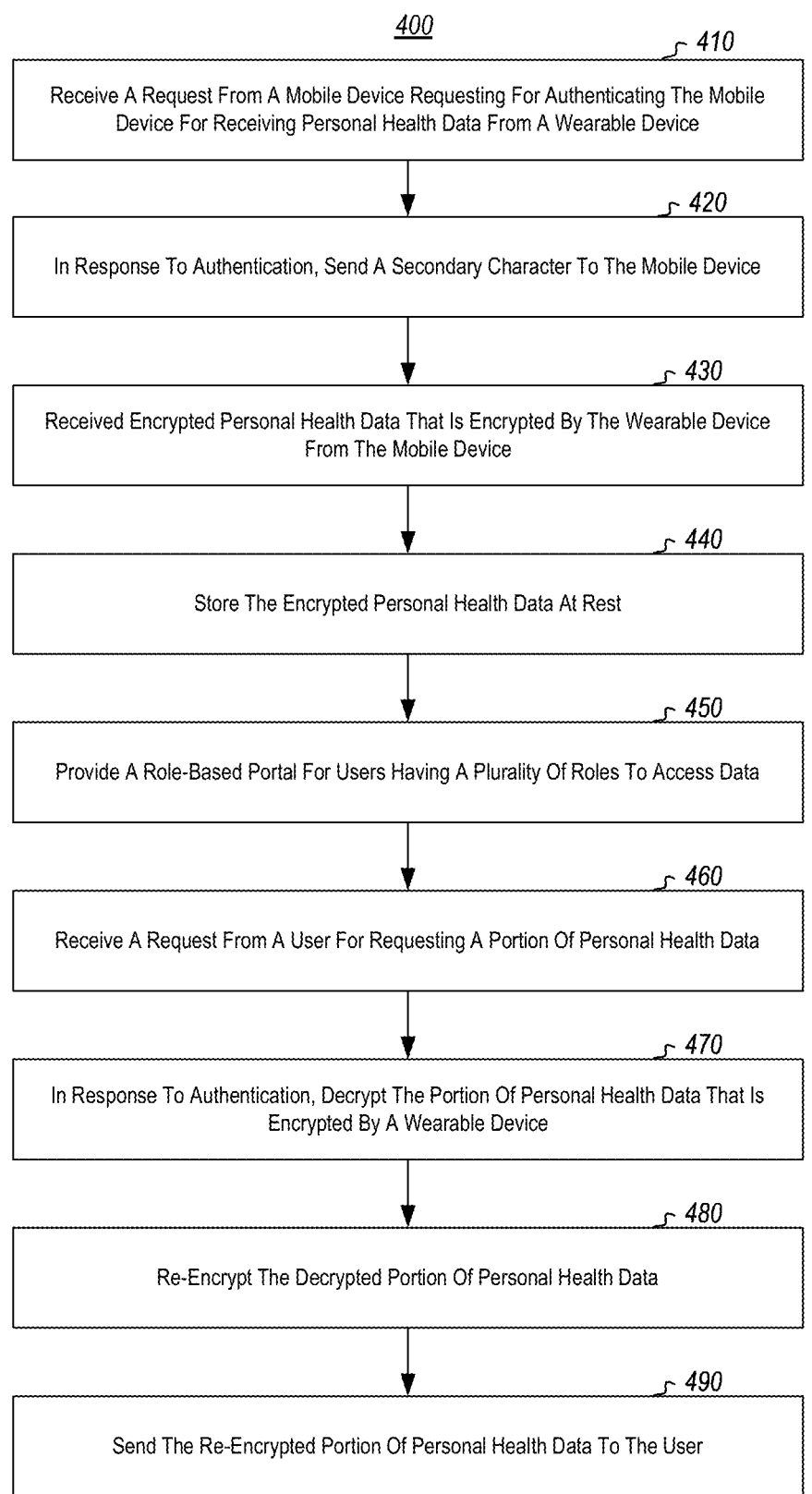
FIG. 4 illustrates a flowchart of an example method for storing and providing encrypted personal health data to users having different roles.

FIG. 4 illustrates a flowchart of an example method 400 for storing and providing encrypted personal health data, which may be performed by a cloud service (e.g., the monitoring platform 110, cloud service 230, or the cloud service 360). The method 400 includes receiving a request from a mobile device requesting for authenticating the mobile device for receiving personal health data from a wearable device (act 410). In response to authentication, a secondary character is sent to the mobile device (act 420). After receiving the secondary character, the mobile device passes the secondary character to the wearable device. After successful verification, the wearable device encrypts a set of personal health data with a device encryption key and sends the encrypted personal health data to the mobile device. The mobile device then passes the encrypted personal health data to the cloud server. Receiving the encrypted personal health data that is encrypted by the wearable device from the mobile device (act 430), the cloud service stores the encrypted personal health data at rest (act 440).

The cloud service further provides a role-based portal for users having a plurality of roles to access different portions of personal health data (act 450). A user at a portal may request a portion of personal health data (act 460). After receiving the request from the user, the cloud service authenticates the user and decrypts the portion of personal health data that is encrypted by a wearable device (act 470) and re-encrypts the decrypted portion of personal health data via a different encryption mechanism (act 480). The re-encrypted portion of personal health data is then sent to the user (act 490). In response to receiving the portion of the encrypted personal health data, the user's device or browser is able to decrypt the encrypted personal health data and display the decrypted personal health data in the browser.

Figure 5:
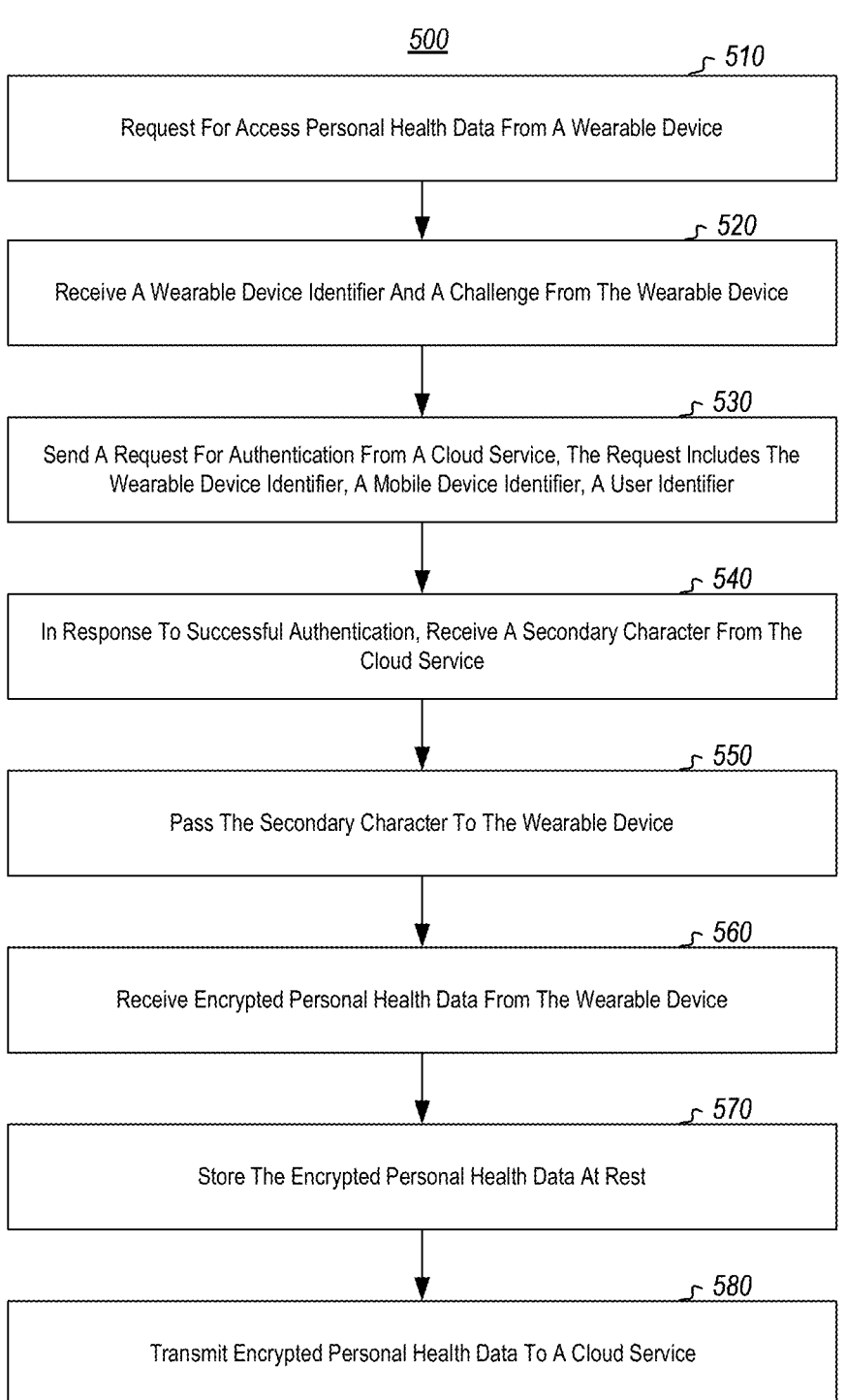
FIG. 5 illustrates a flowchart of an example method for receiving from a wearable device and transmitting to a cloud service encrypted personal health data.

FIG. 5 illustrates a flowchart of an example method 500 for receiving and transmitting encrypted personal health data, which may be performed by a mobile device of a patient (e.g., the mobile device 170 of FIG. 1, the smart mobile device 220 of FIG. 2, and care patient app 330 of FIG. 3). The method 500 includes requesting access to personal health data from a wearable device (act 510) and receiving a wearable device identifier and a challenge from the wearable device (act 520). In response to receiving the wearable device identifier and the challenge, the mobile device sends a request for authentication from a cloud service (act 530). The request includes the wearable device identifier, a mobile device identifier, and a user identifier. In response to successful authentication, the mobile device receives a secondary character from the cloud service (act 540) and passes the secondary character to the wearable device (act 550). In response to receiving the secondary character, the wearable device determines whether the challenge is properly responded. In response to successfully verifying the secondary character, the wearable device sends the encrypted personal health data to the mobile device. Receiving the encrypted personal health data from the wearable device (act 560), the mobile device stores the encrypted personal health data as encrypted data at rest (act 570), and then transmits the encrypted personal health data to a cloud service (act 580).

Although the subject matter has been described in language specific to structural features and/or methodological acts, it is to be understood that the subject matter defined in the appended claims is not necessarily limited to the described features or acts described above, or the order of the acts described above. Rather, the described features and acts are disclosed as example forms of implementing the claims.

The present invention may comprise or utilize a special-purpose or general-purpose computer system that comprises computer hardware, such as, for example, one or more processors and system memory, as discussed in greater detail below. Configurations within the scope of the present invention also comprise physical and other computer-readable media for carrying or storing computer-executable instructions and/or data structures. Such computer-readable media can be any available media that can be accessed by a general-purpose or special-purpose computer system. Computer-readable media that store computer-executable instructions and/or data structures are computer storage media. Computer-readable media that carry computer-executable instructions and/or data structures are transmission media. Thus, by way of example, and not limitation, configurations of the invention can comprise at least two distinctly different kinds of computer-readable media: computer storage media and transmission media.

Computer storage media are physical storage media that store computer-executable instructions and/or data structures. Physical storage media comprise computer hardware, such as RAM, ROM, EEPROM, solid state drives ("SSDs"), flash memory, phase-change memory ("PCM"), optical disk storage, magnetic disk storage or other magnetic storage devices, or any other hardware storage device(s) which can be used to store program code in the form of computer-executable instructions or data structures, which can be accessed and executed by a general-purpose or special-purpose computer system to implement the disclosed functionality of the invention.

Transmission media can comprise a network and/or data links which can be used to carry program code in the form of computer-executable instructions or data structures, and which can be accessed by a general-purpose or special-purpose computer system. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer system, the computer system may view the connection as transmission media. Combinations of the above should also be comprised within the scope of computer-readable media.

Further, upon reaching various computer system components, program code in the form of computer-executable instructions or data structures can be transferred automatically from transmission media to computer storage media (or vice versa). For example, computer-executable instructions or data structures received over a network or data link can be buffered in RAM within a network interface module (e.g., a "NIM"), and then eventually transferred to computer system RAM and/or to less volatile computer storage media at a computer system. Thus, it should be understood that computer storage media can be comprised in computer system components that also (or even primarily) utilize transmission media.

Computer-executable instructions comprise, for example, instructions and data which, when executed at one or more processors, cause a general-purpose computer system, special-purpose computer system, or special-purpose processing device to perform a certain function or group of functions. Computer-executable instructions may be, for example, binaries, intermediate format instructions such as assembly language, or even source code.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The invention may also be practiced in distributed system environments where local and remote computer systems, which are linked (either by hardwired data links, wireless data links, or by a combination of hardwired and wireless data links) through a network, both perform tasks. As such, in a distributed system environment, a computer system may comprise a plurality of constituent computer systems. In a distributed system environment, program modules may be located in both local and remote memory storage devices.

Those skilled in the art will also appreciate that the invention may be practiced in a cloud computing environment. Cloud computing environments may be distributed, although this is not required. When distributed, cloud computing environments may be distributed internationally within an organization and/or have components possessed across multiple organizations. In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

A cloud-computing model can be composed of various characteristics, such as on-demand self-service, broad network access, resource pooling, rapid elasticity, measured service, and so forth. A cloud computing model may also come in the form of various service models such as, for example, Software as a Service ("SaaS"), Platform as a Service ("PaaS"), and Infrastructure as a Service ("IaaS"). The cloud-computing model may also be deployed using different deployment models such as private cloud, community cloud, public cloud, hybrid cloud, and so forth.

Some configurations, such as a cloud computing environment, may comprise a system that comprises one or more hosts that are each capable of running one or more virtual machines. During operation, virtual machines emulate an operational computing system, supporting an operating system and perhaps one or more other applications as well. In some configurations, each host comprises a hypervisor that emulates virtual resources for the virtual machines using physical resources that are abstracted from view of the virtual machines. The hypervisor also provides proper isolation between the virtual machines. Thus, from the perspective of any given virtual machine, the hypervisor provides the illusion that the virtual machine is interfacing with a physical resource, even though the virtual machine only interfaces with the appearance (e.g., a virtual resource) of a physical resource. Examples of physical resources including processing capacity, memory, disk space, network bandwidth, media drives, and so forth.

For the processes and methods disclosed herein, the operations performed in the processes and methods may be implemented in differing order. Furthermore, the outlined operations are only provided as examples, and some of the operations may be optional, combined into fewer steps and operations, supplemented with further operations, or expanded into additional operations without detracting from the essence of the disclosed embodiments.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A service computer system, comprising:
one or more processors; and
one or more computer-readable hardware storage devices having stored thereon computer-executable instructions that are structured such that, when executed by the one or more processors, the computer-executable instructions configure the computing system to perform at least the following:
receive a request from a mobile device requesting authentication of the mobile device, the mobile device being configured to receive, after authentication, personal health data from a wearable device that is registered with the service computer system, the request including a wearable device identifier, a mobile device identifier, and a user identifier;
in response to the request for authentication of the mobile device, send a secondary character to the mobile device for passing the secondary character to the wearable device, wherein successful verification of the secondary character by the wearable device causes the wearable device to send a set of encrypted personal health data to the mobile device, and causes the mobile device to pass the encrypted personal health data to the service computer system;
receive the encrypted personal health data from the mobile device; and
store the encrypted personal health data as encrypted data.

2. The service computer system of claim 1, further configured to:

provide a role-based portal to users having a plurality of roles.

3. The service computer system of claim 2, wherein the plurality of roles includes (1) an admin role, (2) a clinical role, (3) a patient role, and (4) a reviewer role, and each of the plurality of roles is given a different scope of permission in operating on a different portion of personal health data.

4. The service computer system of claim 3, wherein the role-based portal provides a web application configured to allow users having the plurality of roles to access personal health data at a web browser.

5. The service computer system of claim 3, wherein the role-based portal is configured to:
receive a request for a portion of personal health data from a user having a particular role among the plurality of roles at a web browser;
authenticate the request based on a user identifier and a device identifier; and
provide the requested personal health data to the web browser.

6. The service computer system of claim 5, wherein providing the requested personal health data to the web browser comprises:
decrypt encrypted personal health data that was encrypted by a wearable device via a first encryption mechanism;
re-encrypt the decrypted personal health data via a second encryption mechanism; and
send the re-encrypted personal health data to the web browser.

7. The service computer system of claim 6, wherein the wearable device has an encryption key configured to encrypt the personal health data via the first encryption mechanism, and the service computer system also has the encryption key configured to decrypt the personal health data via the first encryption mechanism.

8. The service computer system of claim 5, further configured to:
receive a request from a second mobile device requesting for authenticating the second mobile device, the request including a second device identifier and a second user identifier;
in response to authenticating the second device identifier and the second user identifier, send a second character to the second mobile device, causing the second device to receive a second set of encrypted personal health data from a second wearable device and pass the second set of encrypted personal health data to the service computer system;
receive the second set of encrypted personal health data from the mobile device;
store the second set of encrypted personal health data as encrypted at rest.

9. The service computer system of claim 8, a first wearable device has a first encryption key, and the second wearable device has a second encryption key that is different from the first encryption key, such that when the first encryption key is compromised, the personal health data encrypted by the second key is still intact.

10. The service computer system of claim 8, further configured to:
anonymize the personal health data received from the mobile device; and
send the anonymized personal health data to a data processing service.

11. A mobile device, comprising:
one or more processors; and one or more computer-readable hardware storage devices having stored thereon computer-executable instructions that are structured such that, when executed by the one or more processors, the computer-executable instructions configure the mobile device to perform the following:

send a request for personal health data to a wearable device via a personal area network;

receive a wearable device identifier from the wearable device;

send an authentication request to a cloud service with a user identifier, a mobile device identifier, and the wearable device identifier;

in response to successful authentication, receiving a second character from the cloud service;

provide the second character to the wearable device;

in response to successfully verifying the second character by the wearable device, receive encrypted personal health data of a patient from the wearable device;

store encrypted personal health data at rest associated; and pass the encrypted personal health data to a cloud service.

12. The mobile device of claim 11, further configured to:

request personal health data from the cloud service;

in response to successful authentication, receive encrypted personal health data from the cloud service; and decrypt the encrypted personal health data to display the decrypted personal health data.

13. The mobile device of claim 11, wherein the encrypted personal health data received from the wearable device was encrypted via a first encryption mechanism that cannot be decrypted by the mobile device, and the encrypted personal health data received from the cloud service is encrypted via a second encryption mechanism that is able to be decrypted by the mobile device.

* * * * *